United States Patent [19]

Shibagaki et al.

[11] Patent Number: 5,420,286
[45] Date of Patent: May 30, 1995

[54] OPTICAL RESOLUTION METHOD OF A NICOTINE DERIVATE

[75] Inventors: Makoto Shibagaki; Kyoko Takahashi; Hideyuki Kuno; Hajime Matsushita, all of Yokohama, Japan

[73] Assignee: Japan Tobacco Incorporated, Tokyo, Japan

[21] Appl. No.: 163,531

[22] Filed: Dec. 9, 1993

[30] Foreign Application Priority Data

Dec. 10, 1992 [JP] Japan .................. 4-330413

[51] Int. Cl.⁶ .......................... C07D 401/00
[52] U.S. Cl. ...................... 546/281; 546/282
[58] Field of Search ................ 546/282, 281

[56] References Cited

U.S. PATENT DOCUMENTS

| | | | |
|---|---|---|---|
| 2,315,314 | 3/1943 | Burger et al. | 546/281 |
| 3,644,176 | 2/1972 | Squires et al. | 435/118 |
| 3,915,714 | 10/1975 | Saleck et al. | 430/564 |
| 4,321,387 | 3/1982 | Chavdarian et al. | 546/281 |
| 5,254,543 | 10/1993 | Hanks et al. | 546/281 |

FOREIGN PATENT DOCUMENTS 61-36835 8/1986 Japan.
63-2560 1/1988 Japan.

OTHER PUBLICATIONS

Chemical Abstracts, vol. 79, No. 23, abstract No. 136957 (1973).
Chemical Abstracts, vol. 109, No. 14, abstract No. 121772 (1987).
Chemical Abstracts, vol. 97, No. 1, abstract No. 6716 (1982).
"Biochemistry", 57, 447-471 (1985).
"N-Glycoside of Nicotine Derivative: N-[5-(N'-Methyl-2'-pyrrolidinyl)-2-pyridon]-β-D-glucopyranoside" by A. Ohnishi et al., Agric. Biol. Chem., 46(3), 831-832, 1982.
"The Effects of d-Nicotine and l-Isomer on Nicotinic Receptors" by S. Ikushima et al, The Journal Of Pharmacology And Experimental Therapeutics, vol. 222, No. 2, pp. 463-470 (1982).
"Antinociceptive action of nicotine and its methiodide derivatives in mice and rats" by M. D. Aceto, Br. J. Pharmas. (1983), 79, pp. 869-876.
Chem. Ber., 57B, 1163-1168 (1924).

*Primary Examiner*—C. Warren Ivy
*Assistant Examiner*—A. A. Owens
*Attorney, Agent, or Firm*—Birch, Stewart, Kolasch & Birch

[57] ABSTRACT

Disclosed is a method of obtaining (S)-(−)-3-(1-methyl-2-pyrrolidinyl)-2-pyridone (2) and (R)-(+)-3-(1-methyl-2-pyrrolidinyl)-2-pyridone (3) by resolving a racemic mixture of the compounds (2) and (3). More specifically, disclosed is a method of obtaining the optically active nicotine derivatives (2) and (3) shown below, which comprises steps of binding (±)-3-(1-methyl-2-pyrrolidinyl)-2-pyridone to a sugar derivative, resolving the obtained compound into two types of stereoisomers, and treating them under an acidic condition.

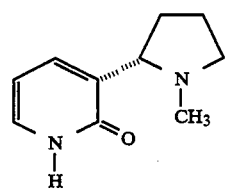

(2)

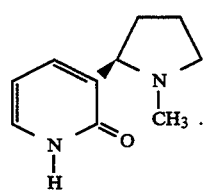

(3)

13 Claims, No Drawings

OPTICAL RESOLUTION METHOD OF A NICOTINE DERIVATE

BACKGROUND OF THE INVENTION

1. Field of the Invention

The present invention relates to a method of resolving (±)3-(1-methyl-2-pyrrolidinyl)-2-pyridone (1) into (S)-(−)-3-(1-methyl-2-pyrrolidinyl)-2-pyridone (2) and (R)-(+)-3-(1-methyl-2-pyrrolidinyl)-2-pyridone (3).

2. Description of the Related Art

Nicotine is an alkaloid which can be obtained as a by-product in the tobacco industry and a derivative thereof is also known as a useful compound having an effect of improving the flavor and taste of tobacco (e.g., Jpn. Pat. Nos. 1371806 and 1456909). More specifically, it has been found that glycosides, which are composed of optically active nicotine derivatives (2) and (3) and glucose etc. binding thereto, are remarkably effective in improving the flavor and taste of tobacco. These derivatives (2) and (3) are not only important intermediates to produce the aforementioned useful compounds but also compounds whose own physiological activities are expected.

In order to synthesize the compounds (2) and (3), first, a racemic mixture of the compounds (2) and (3) are synthesized by use of a known method, and then the racemic mixture obtained must be optically resolved. However, the optical resolution method has a drawback in that the cost to produce the compounds (2) and (3) on an industrial scale is inevitably increased since an optically active column, which is a high-cost and requires a high dilution condition at a resolution process, must be used in this method.

SUMMARY OF THE INVENTION

The present invention has been made in view of the above circumstances. The object of the present invention is to provide an economical method of resolving optically active nicotine derivatives (2) and (3) from a racemic mixture thereof on an industrial scale.

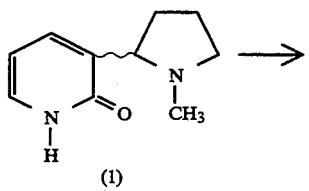

(1)

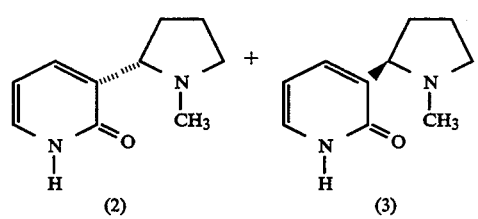

The object of the present invention can be achieved by the following methods (A), (B), and (C).

<Method (A)>

This is a method of optically resolving (±)-3-(1-methyl-2-pyrrolidinyl)-2-pyridone (1) into (S)-(−)-3-(1-methyl-2-pyrrolidinyl)-2-pyridone (2) and (R)-(+)-3-(1-methyl-2-pyrrolidinyl)-2-pyridone (3), and comprises the steps of (i) obtaining a nicotine glycoside (5), which is a diastereomer mixture, from (±)-3-(1-methyl-2-pyrrolidinyl)-2-pyridone (1) and hexose (4) as shown below:

(Process i)

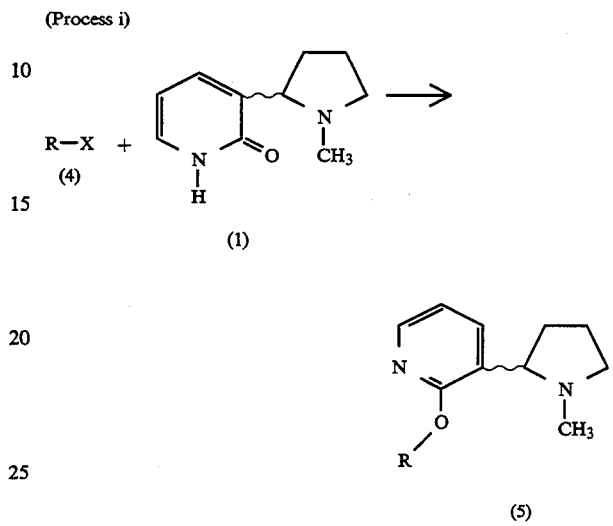

wherein R is a monosaccharide or a disaccharide of hexose whose hydroxyl group is protected by an acyl group, and X is an active unit such as a halogen atom;

(ii) obtaining compounds (6) and (7) by resolving the nicotine glycoside (5) by means of column chromatography as shown below:

(Process ii)

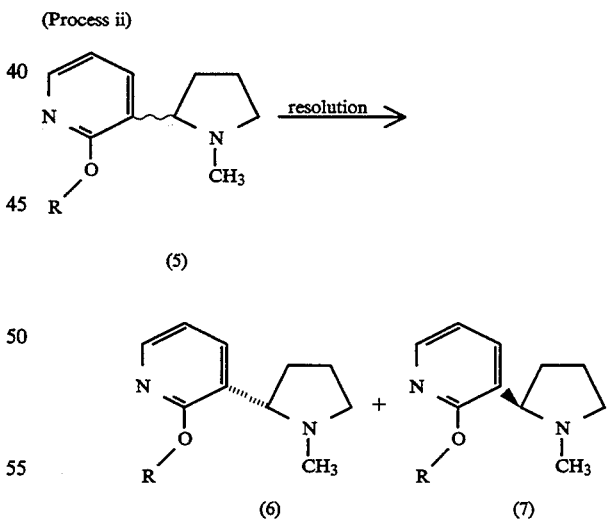

wherein R is defined hereinabove; and (iii) obtaining (S)-(−)-3-(1-methyl-2-pyrrolidinyl)-2-pyridone (2) and (R)-(+)-3-(1-methyl-2-pyrrolidinyl)-2-pyridone (3) by treating the compounds (6) and (7) under an acidic condition, respectively, as shown below:

(Process iii)

-continued

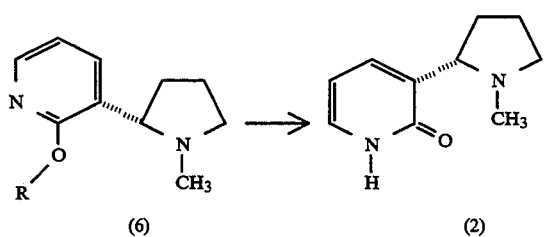
(6) → (2)

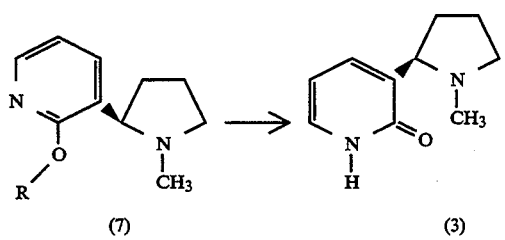
(7) → (3)

wherein R is defined hereinabove.

<Method (B)>

This is a method according to the method (A) in which the step (iii) of the method (A) is replaced by the following step (iii) of deprotecting the compounds (6) and (7) obtained in the aforementioned step (ii) under a basic condition, and treating the deprotected compounds (6) and (7) under an acidic condition to obtain compounds (2) and (3) as shown below:

(Process iii)

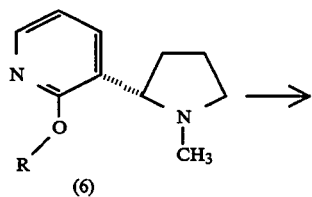
(6) →

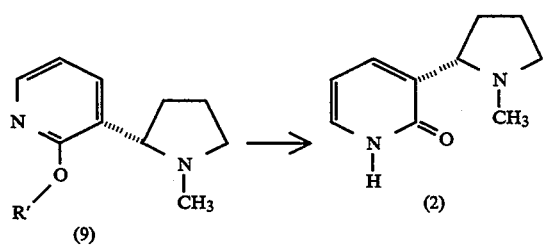
(9) → (2)

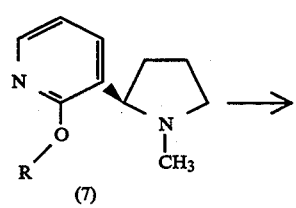
(7) →

-continued

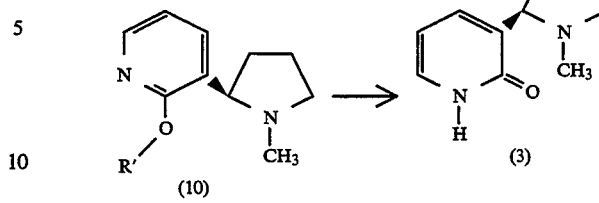
(10) → (3)

wherein R is defined hereinabove and R' is a monosaccharide or a disaccharide of hexose whose hydroxyl group is not protected.

<Method (C)>

This is a method according to the method (A), further comprising the steps (iv) to (vi) in the following which are performed after the aforementioned step (i):

(iv) obtaining a diastereomer mixture (8) by removing the protecting group of the sugar part of the mixture (5) under an alkaline condition as shown below:

(Process iv)

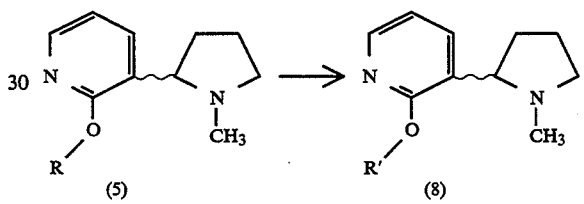
(5) → (8)

wherein R and R' are defined hereinabove;

(v) obtaining compounds (9) and (10) by resolving the diastereomer mixture (8) by means of column chromatography as shown below:

(Process v)

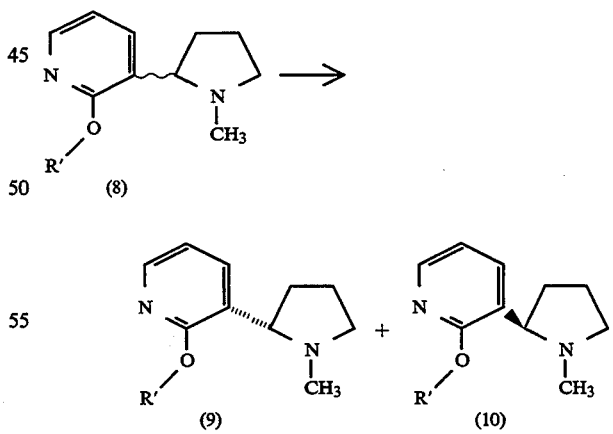
(8) → (9) + (10)

wherein R' is defined hereinabove; and (vi) obtaining (S)-(−)-3-(1-methyl-2-pyrrolidinyl)-2-pyridone (2) and (R)-(+)-3-(1-methyl-2-pyrrolidinyl)-2-pyridone (3) by treating the compounds (9) and (10) under an acidic condition as shown below:

(Process vi)

-continued

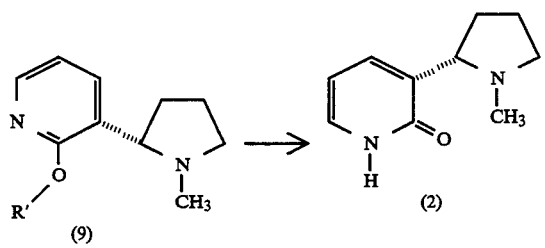

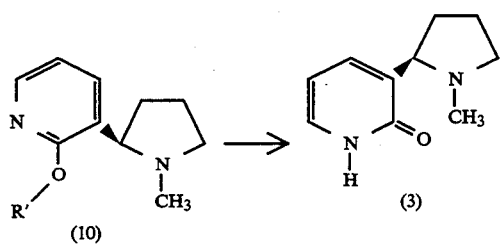

wherein R' is defined hereinabove.

DETAILED DESCRIPTION OF THE PREFERRED EMBODIMENTS

Hereinafter, the present invention will be described in detail.

The present invention is a method of obtaining nicotine derivatives (2) and (3), which comprises steps of obtaining a nicotine glycoside (5), which is a diasteromer, from a racemic mixture (1), and resolving the nicotine glycoside (5) by column chromatography, or comprises steps of obtaining a nicotine glycoside (6) by deprotecting the nicotine glycoside (5), and resolving the nicotine glycoside (6) by column chromatography as shown below:

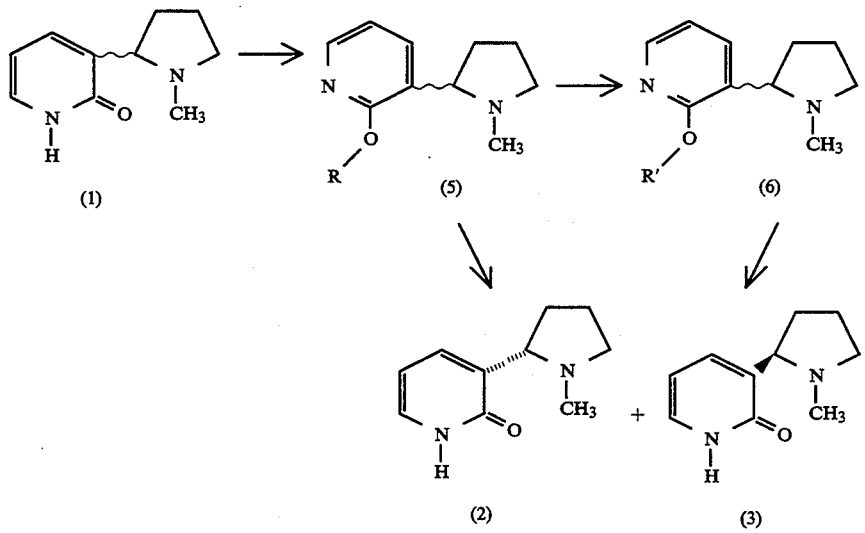

wherein R and R' are defined hereinabove.

In the present invention, an R group of the nicotine glycoside (5) is an appropriately protected sugar derivative. The appropriately protected sugar derivative is a sugar whose hydroxyl group is protected by an appropriate protecting group. In the present invention, the R group is, for example, a monosaccharide or a disaccharide of hexose whose hydroxyl group is protected by an appropriate protecting group. Examples include appropriately protected glucopyranosyl, galactopyranosyl, mannopyranosyl group, and the like for the monosaccharide derivative; or appropriately protected lactosyl, maltosyl, cellobiosyl group, and the like for the disaccharide. Preferably, the R group in the present invention is a monosaccharide since a starting sugar for a preparation of the nicotine derivative (5) is a commercially available and low cost compound and relatively easier to convert into a glycosyl donor.

"An appropriate protecting group" in the present invention is an acyl group. Examples include an alkylcarbonyl group such as an acetyl group and a pivaloyl group; and an arylcarbonyl group such as a benzoyl group and a toluoyl group. Among them, an acetyl group or a benzoyl group is preferable, and an acetyl group is the most preferable.

The term of "appropriately protected" means that the hydroxyl groups on the R group are protected by the above appropriate protecting group. Accordingly, the most preferable R group in the present invention is a 2,3,4,6-tetra-O-acetyl-D-glucopyranosyl group. From the viewpoint of simple synthesis, the R group in the present invention preferably has a glycosidic bond in a β configuration.

Accordingly, as the nicotine glycoside (5) of the present invention, (±)-3-(1-methyl-2-pyrrolidinyl)-2-pyridyl 2,3,4,6-tetra-O-acetyl-D-D-glucopyranoside (5a) is the most preferred.

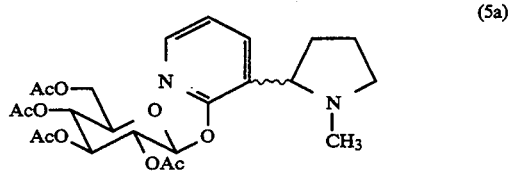

(5a)

Since the nicotine glycoside (6) is obtained by deprotecting the aforementioned glycoside (5), the R' group of the nicotine glycoside (6) is the deprotected R group. Accordingly, as the nicotine glycoside (6), the nicotine glycoside (6a) shown below whose R' group is a glucopyranosyl group is the most preferable.

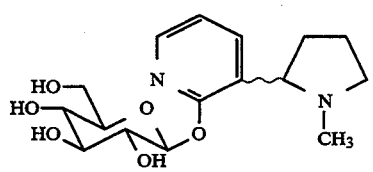

(6a)

The preparation of the nicotine glycosides (5) and (6) will be described in the methods (A) to (C).

Hereinbelow, the methods (A) to (C) of the present invention will be described.

<Method (A)>

The step (i) is a process of obtaining a nicotine glycoside (5), which is a diastereomer mixture, from a glycosyl donor (4) and a nicotine derivative (1).

The glycosyl donor (4) is not particularly restricted as long as the nicotine glycoside (5) obtained in the step (i) can be efficiently resolved by means of column chromatography in the following step.

It is preferred in the present invention that the glycosyl donor (4) is a sugar compound in which the hydroxyl group at the reduced end is replaced by an active unit such as a halogen atom and the other hydroxyl groups are protected by acyl group such as acetyl group, benzoyl group and the like.

The above-mentioned preferable glycosyl donor (4) can be readily obtained by halogenating the glycosyl compound which has a hydroxyl group on the reduced end position unprotected or protected by an acyl group which can be readily converted into an active unit, with the other hydroxyl groups being protected by an acyl group. As the halogenating agent in the present invention, hydrobromic acid—acetic acid solution, carbon tetrachloride—tris(dimethylamino)phosphine, or the like may be used. A preferable halogen atom in the present invention may be fluorine, chloride, or bromide, but from the reactivity point of view, bromide is the most preferable.

As a second step, the glycosyl donor (4) and the nicotine derivative (1) are subjected to a glycosylation reaction. 3-(1-methyl-2-pyrrolidinyl)-2-pyridone (1) and the glycosyl donor (4) are dissolved in an appropriate solvent, and then the glycosylation reaction is carried out in the presence of a promoter.

Although the type of solvent used in the reaction is not particularly restricted as long as it is used in general glycosylation, chloroform or methylene chloride is preferably used.

The promoter used in the reaction is not particularly restricted as long as the glycoside (5) can be efficiently obtained in the presence thereof. When the active unit of the glycosyl donor (4) is a halogen, a silver compound such as silver carbonate and silver trifluoromethanesulfonic acid is preferably used.

The step (ii) is a process in which the glycoside (5), which is the diastereomer mixture obtained in the above step (i), is resolved into the compounds (6) and (7) shown below:

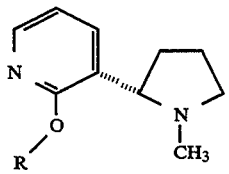

(6)

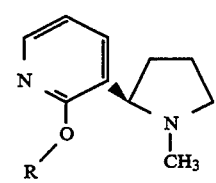

(7)

wherein R is defined hereinabove.

The resolution of the mixture (5) can be carried out by subjecting the mixture (5) to column chromatography, followed by extracting with an appropriate solvent. The column chromatography used in this step is not particularly restricted as long as the mixture (5) can be resolved into the optically active compounds (6) and (7). For example, an optically active column, an ODS reversed phase column, an alumina column, and a silica gel column, all can be used in the chromatography.

A developing solvent can be appropriately chosen according to the column chromatography to be used. For example, a solvent such as ethyl acetate is preferable when silica gel column chromatography is employed.

Column chromatography may be carried out under normal atmospheric pressure or under low pressure which is nevertheless not quite as low as normal atmospheric pressure as in the case of so-called flash column chromatography. Pressure used in the column chromatography is not particularly restricted and can be chosen according to the column chromatography employed.

The step (iii) is a process in which the desired compounds (2) and (3) are obtained from the optically active compounds (6) and (7) obtained in the step (ii).

In this step (iii), the compounds (6) and (7) are each dissolved in an appropriate solvent, and the glycosidic bond of each of the dissolved compounds is cleaved under an acidic condition.

Although the solvent used in this reaction is not particularly restricted as long as it is stable under an acidic condition, a solvent such as methanol is preferably used.

Although the acid catalyst used in this reaction is not particularly restricted as long as it can cleave the glycosidic bond, hydrochloric acid, sulfuric acid, and nitric acid may be mentioned.

After being neutralized, the reaction mixture can be purified by means of column chromatography, if necessary.

In this way, the optically active compounds (2) and (3) can be obtained in a high yield.

<Method (B)>

This method is a process of obtaining optically active compounds (2) and (3), which comprises steps of hydrolytically removing the protecting group of compounds (6) and (7) obtained in the step (ii) of the method (A) to prepare the following compounds (9) and (10), and cleaving the glycosidic bond of the compounds (9) and (10) under an acidic condition.

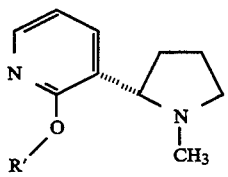

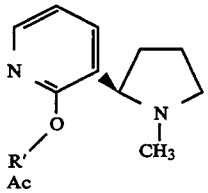

wherein R' is defined hereinabove.

The compounds (6) and (7) are dissolved in an appropriate solvent and hydrolyzed under a basic condition.

Although the solvent is not particularly restricted as long as it is used for a general hydrolysis under a basic condition, methanol, ethanol, and the like may be mentioned.

Although the base is not particularly restricted as long as it can remove the acyl group of a glycoside derivative, sodium methoxide, sodium hydroxide, ammonia, and the like may be used.

The desired compounds (2) and (3) can be obtained by treating the above-obtained compounds (9) and (10) under the same acidic condition as in the step (iii) of the method (A).

<Method (C)>

This method is a process of obtaining the compounds (2) and (3), which comprises steps of preparing a nicotine glycoside (8), which is a diastereomer mixture, from the nicotine glycoside (5) obtained in the step (i) of the method (A), resolving the nicotine glycoside (8) into compounds (9) and (10) by means of column chromatography, and thereafter cleaving the glycosidic bond of the compounds (9) and (10).

The nicotine glycoside (5) can be synthesized in the same procedure as in the step (i) of the method (A).

The step (iv) is a process in which the nicotine glycoside (8), which is a diastereomer mixture, is obtained by hydrolyzing the nicotine glycoside (5) obtained in the step (i) under a basic condition. In this process, the nicotine glycoside (5) is dissolved in an appropriate solvent, and then treated with a base.

Although the solvent is not particularly restricted as long as it is used for a general hydrolysis in a basic condition, methanol, ethanol and the like may be mentioned as examples.

Although the base is not particularly restricted as long as it can remove the acyl group of compound (5), sodium methoxide, sodium hydroxide, ammonia, and the like are preferable.

The step (v) is a process of resolving the nicotine glycoside (8) obtained in the step (iv) into the compounds (9) and (10).

The nicotine glycoside (8) can be resolved by means of column chromatography and then extracted with an appropriate solvent. The column chromatography to be used is not particularly restricted as long as it can resolve the nicotine glycoside (8) into the optically active compounds (9) and (10). For example, optically active column, an ODS reversed phase column, alumina column, and a silica gel column, all can be used in the chromatography.

A developing solvent can be appropriately chosen according to the column chromatography to be employed. For example, a chloroform—methanol mixed solvent is preferable when silica gel column chromatography is employed.

Column chromatography may be carried out under normal atmospheric pressure or under low pressure which is nevertheless not quite as low as normal atmospheric pressure as in the case of so-called flash column chromatography. The pressure used in column chromatography is not particularly restricted and can be chosen according to the column chromatography to be employed.

The step (vi) is a process of obtaining the desired compounds (2) and (3) from optically active compounds (9) and (10) obtained in the step (v).

In this step (vi), the desired compounds (2) and (3) can be obtained by treating the compounds (9) and (10) in the same procedure as in the step (iii) of the method (A).

Hereinbelow, the methods (A) to (C) will be described specifically with reference to the preferable compounds (5a) and (6a) of the present invention.

In the following description, an abbreviation of Ac represents an acetyl group.

<Method (A)>

In the step (i), a nicotine glycoside (5a) can be obtained. (±)3-(1-methyl-2-pyrrolidinyl)-2-pyridone (1) and a glycosyl donor, 2,3,4,6-tetra-O-acetyl-D-glucopyranosyl bromide (4a), are dissolved in a solvent such as methylene chloride and allowed to react in the presence of a promoter such as silver carbonate to obtain the nicotine glycoside (5a). The glycosyl donor (4a) can be prepared by the method disclosed in Chem. Ber., 57B, 1163 (1924).

(Process i)

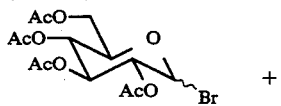

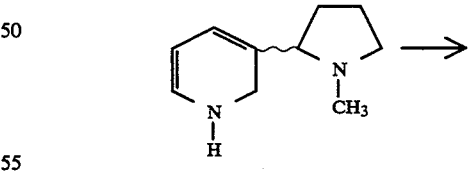

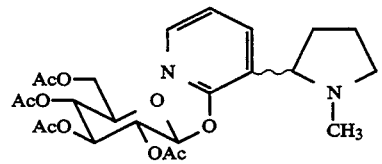

In the step (ii), the nicotine glycoside (5a), which is the diastereomer mixture obtained in the step (i), is resolved into the compounds (6a) and (7a) shown below.

(Process ii)

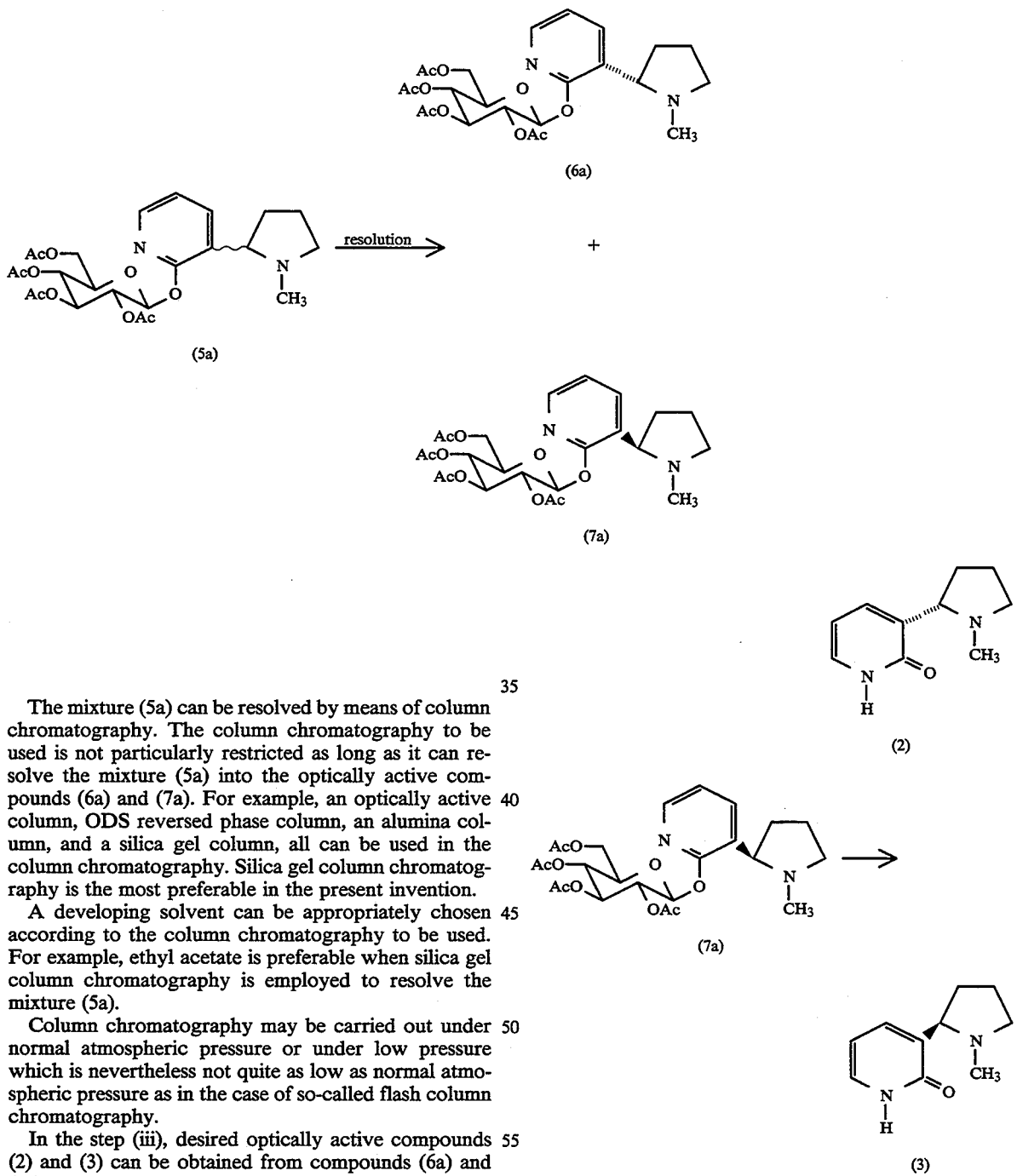

The mixture (5a) can be resolved by means of column chromatography. The column chromatography to be used is not particularly restricted as long as it can resolve the mixture (5a) into the optically active compounds (6a) and (7a). For example, an optically active column, ODS reversed phase column, an alumina column, and a silica gel column, all can be used in the column chromatography. Silica gel column chromatography is the most preferable in the present invention.

A developing solvent can be appropriately chosen according to the column chromatography to be used. For example, ethyl acetate is preferable when silica gel column chromatography is employed to resolve the mixture (5a).

Column chromatography may be carried out under normal atmospheric pressure or under low pressure which is nevertheless not quite as low as normal atmospheric pressure as in the case of so-called flash column chromatography.

In the step (iii), desired optically active compounds (2) and (3) can be obtained from compounds (6a) and (7a).

(Process iii)

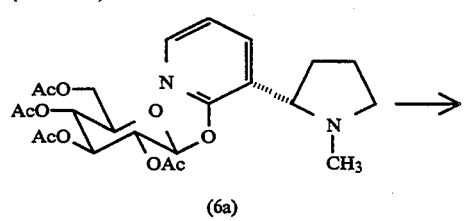

The compounds (6a) and (7a) are dissolved in a solvent such as methanol, respectively, and allowed to react in the presence of hydrochloric acid etc. After being neutralized, the resulting reaction mixture may be purified by means of column chromatography, if necessary.

In this way, the optically active compounds (2) and (3) can be obtained in a high yield.

<Method (B)>

This method is a process of obtaining optically active compounds (2) and (3), which comprises steps of hydrolyrically removing the protecting group of the compound (6a) and (7a) obtained in the step (ii) of the method (A) to obtain compounds (9a) and (10a), and cleaving the glycosidic bond of the compounds (9a) and (10a) under an acidic condition.

The compounds (6a) or (7a) is dissolved in an alcohol such as methanol and ethanol, and hydrolyzed with a base such as sodium methoxide, sodium hydroxide, and ammonia.

Thus obtained compounds (9a) and (10a) are treated under the same acidic condition as in the step (iii) of the method (A) to obtain the desired compounds (2) and (3).

(Process i)

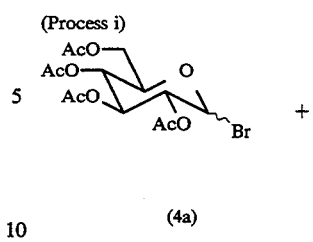

(4a)

(Process iii)

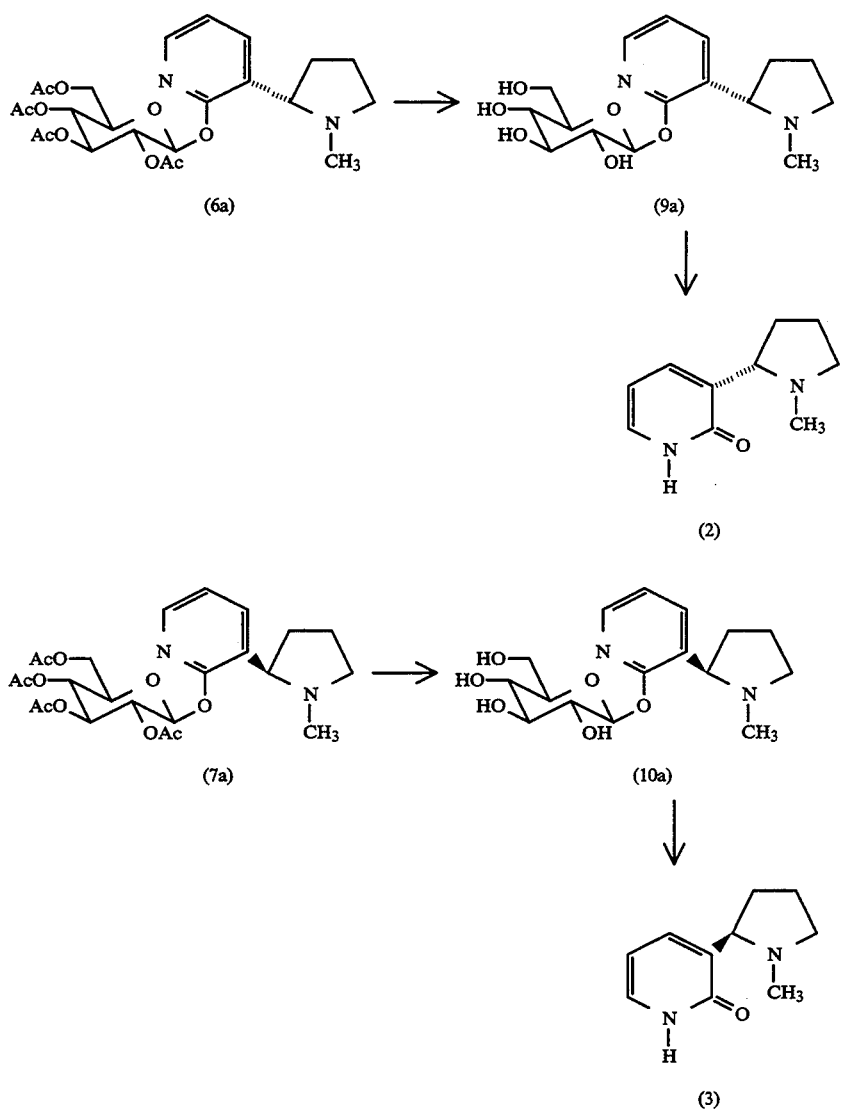

<Method (C)>

In this method, the nicotine glycoside (5a) obtained in the step (i) of the method (A) is hydrolyzed to obtain the nicotine glycoside (8a), which is a diastereomer mixture. The nicotine glycoside (8a) is resolved by means of column chromatography to obtain the compound (9a) and (10a), and then the glycosidic bond of the compounds (9a) and (10a) is cleaved to obtain the compounds (2) and (3), respectively.

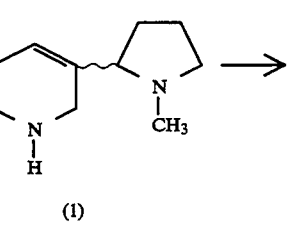

(1)

-continued

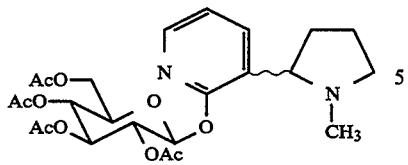

(5a)

The nicotine glycoside (5a) can be synthesized in the same procedure as in the step (i) of the method (A).

The step (iv) is a process in which the nicotine glycoside (8a), which is a diastereomer mixture, is obtained by hydrolyzing the nicotine glycoside (5a) obtained in the step (i) under a basic condition. In this process, the nicotine glycoside (5a) is dissolved in an appropriate solvent, and then treated with a base.

More specifically, the compounds (5a) is dissolved in an alcohol such as methanol and ethanol and then hydrolyzed with a base such as sodium methoxide, sodium hydroxide, and ammonia.

(Process iv)

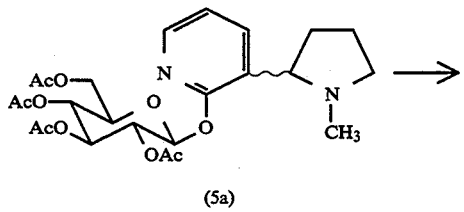

(5a)

-continued

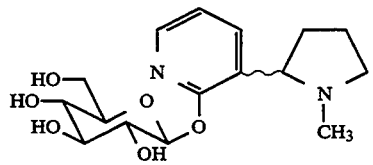

(8a)

The step (v) is a process in which the nicotine glycoside (8a), which is the diasteromer mixture obtained in the step (iv), is resolved into the compounds (9a) and (10a).

The mixture (8a) may be resolved by means of column chromatography. The column chromatography is not particularly restricted as long as it can resolve the mixture (8a) into the optically active compounds (9a) and (10a). For example, an optically active column, an ODS reversed phase column, an alumina column, and a silica gel column, all can be used in the column chromatography.

A developing solvent can be appropriately chosen according to the column chromatography to be used. For example, a chloroform—methanol mixed solvent is preferable when the silica gel column chromatography is employed to resolve the mixture (8a).

Column chromatography may be carried out under normal atmospheric pressure or under low pressure which is nevertheless not quite as low as normal atmospheric pressure as in the case of so-called flash column chromatography.

(Process v)

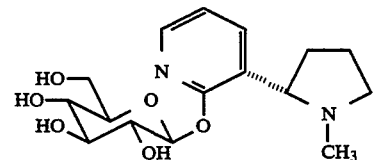

(9a)

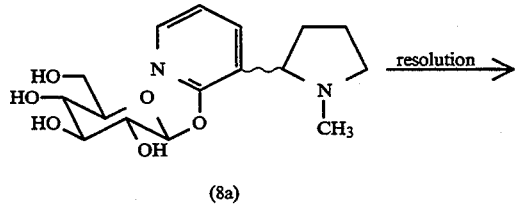

(8a) resolution →  +

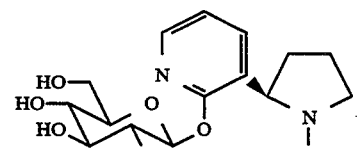

(10a)

In the step (vi), the desired optically active compounds (2) and (3) can be obtained from the compounds (9a) and (10a).

In this step, the optically active compounds (9a) and (10a) can be treated in the same procedure as in the step (iii) of the method (A) to obtain the desired compounds (2) and (3).

(Process vi)

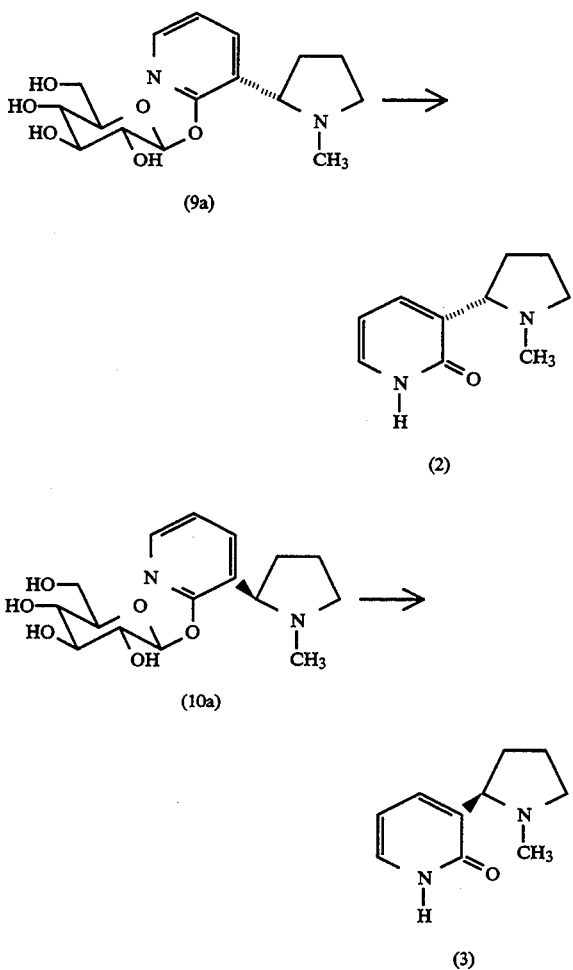

In this way, the optically active compounds (2) and (3) can be obtained in a high yield.

Hereinbelow, the present invention will be further described by example, which should not be construed as limiting the scope of the present invention.

(±)3-(1-methyl-2-pyrrolidinyl)-2-pyridone (1) [Nature, 165, 369 (1950)] and 2,3,4,6-tetra-O-acetyl-glucopyranosyl bromide (4a) [Chem. Ber., 573, 1163 (1924)] were synthesized by a known method.

EXAMPLE 1

Preparation of
(±)-3-(1-methyl-2-pyrrolidinyl)-2-pyridyl
2,3,4,6-tetra-O-acetyl-β-D-glucopyranoside (5a)

(±)-3-(1-methyl-2-pyrrolidinyl)-2-pyridone (1)(2.0 g) and 2,3,4,6-tetra-O-acetylglucopyranosyl bromide (4a)(5.6 g) were dissolved in dichloromethane (40 ml). To this solution, silver carbonate (1.8 g) was added. The mixture was stirred at room temperature for 24 hours while the vessel was shielded from light by an aluminum sheet. Solid material was filtered off, and the filtrate was concentrated under reduced pressure. As a result, (±)-3-(1-methyl-2-pyrrolidinyl)-2-pyridyl 2,3,4,6-tetra-O-acetyl-β-D-glucopyranoside (5a) was obtained. The compound (5a) obtained as above was subjected to the experiment of the following example without purification.

EXAMPLE 2

Preparation of
(S)-(−)-3-(1-methyl-2-pyrrolidinyl)-2-pyridyl
2,3,4,6-tetra-O-acetyl-β-D-glucopyranoside (6a) and
(R)-(+)-3-(1-methyl-2-pyrrolidinyl)-2-pyridyl
2,3,4,6-tetra-O-acetyl-β-D-glucopyranoside (7a)

The diastereomer mixture (5a) was resolved by means of silica gel column chromatography using ethyl acetate as an eluent. As a result, (S)-(−)-3-(1-methyl-2-pyrrolidinyl)-2-pyridyl 2,3,4,6-tetra-O-acetyl-β-D-glucopyranoside (6a) and (R)-(+)-3-(1-methyl-2-pyrrolidinyl)-2-pyridyl 2,3,4,6-tetra-O-acetyl-β-D-glucopyranoside (7a) were obtained in white-solid form and in yields of 1.8 g and 1.7 g, respectively. Further, (S)-(−)-3-(1-methyl-2-pyrrolidinyl)-2-pyridyl 2,3,4,6-tetra-O-acetyl-β-D-glucopyranoside (6a) and (R)-(+)-3-(1-methyl-2-pyrrolidinyl)-2-pyridyl 2,3,4,6-tetra-O-acetyl-β-D-glucopyranoside (7a) were each recrystallized from ethyl acetate-hexane. As a result, highly purified (S)-(−)-3-(1-methyl-2-pyrrolidinyl)-2-pyridyl 2,3,4,6-tetra-O-acetyl-β-D-glucopyranoside (6a) and (R)-(+)-3-(1-methyl-2-pyrrolidinyl)-2-pyridyl 2,3,4,6tetra-O-acetyl-β-D-glucopyranoside (7a) were obtained in yields of 1.7 g (30%) and 1.6 g (28%), respectively.

<Physical properties of the compound (6a)>
Melting point: 149.0°–151.0° C.
$[\alpha]_D$ −68.1° (c 0.75, MeOH)
IR: $\nu(cm^{-1})$; 2948, 2784, 1756, 1589, 1437, 1367, 1230
$^1$H-NMR: δ(CDCl$_3$; ppm from TMS) 1.5–1.6 (1H, m), 1.8–1.9 (2H, m), 1.98 (3H, s), 2.04 (3H, s), 2.05 (6H, s), 2.15 (3H, s), 2.32 (2H, m), 3.20 (1H, ddd, J=2.4, 6.9, 9.2Hz), 3.25 (1H, t, J=8.3Hz), 3.96 (1H, ddd, J=2.3, 4.3, 9.9Hz), 4.14 (1H, dd, J=2.3, 12.4Hz), 4.31 (1H, dd, J=4.3, 12.4Hz), 5.23 (1H, m), 5.36 (2H, m), 6.14 (1H, d, J=8.0Hz), 7.01 (1H, dd, J=4.9, 7.4Hz), 7.83 (1H, dd, J=1.9, 7.4Hz), 8.02 (1H, dd, J=1.9, 4.9Hz)
$^{13}$C-NMR: δ(CDCl$_3$; ppm from TMS); 20.8 (CH$_3$), 23.0 (CH$_2$), 33.7(CH$_2$), 40.8 (CH$_3$) 57.1 (CH$_2$), 61.9 (CH$_2$), 63.1 (CH), 68.5(CH), 71.0 (CH), 72.2 (CH), 73.3 (CH), 93.8 (CH), 119.5 (CH), 127.0 (C), 136.9 (CH) 144.7 (CH), 159.4 (C), 169.4 (C), 169.7 (C), 170.4 (C), 170.8 (C)
MS (%): 509 (M+1)(19), 508 (17), 389 (22), 179(18), 178(19), 177(100), 169(25), 163(20), 109(20), 84(42)

<Physical properties of the compound (7a)>
Melting point: 132.5°–134.0° C.
$[\alpha]_D$+46.4° (c 0.64, MeOH)
IR: $\nu(cm^{-1})$; 2948, 2786, 1756, 1589, 1437, 1369, 1232, 1040, 911, 733, 600
$^1$H-NMR: δ(CDCl$_3$; ppm from TMS) 1.35–1.45 (1H, m), 1.75–1.85 (2H, m), 1.98 (3H, s), 2.01 (3H, s), 2.05 (3H, s), 2.06 (3H, s), 2.10–2.20 (1H, m) 2.23 (3H, S), 2.35 (1H, q, J=8.8 Hz), 3.19 (1H, m), 3.47 (1H, t, J=8.2Hz), 3.96 (1H, m), 4.13 (1H, dd, 12.4Hz), 4.32 (1H, dd, J=4.4, 12.4Hz), 5.22 (1H, t, J=9.2Hz), 5.35 (2H, m,), 6.20 (1H, d, J=7.6Hz), 7.00 (1H, dd, J=4.9, 7.4Hz), 7.84 (1H, dd, J=1.9, 7.4Hz), 8.01 (1H, dd, J=1.9, 4.9Hz)
$^{13}$C-NMR: δ(CDCl$_3$; ppm from TMS); 20.8 (CH$_3$), 22.9 (CH$_2$), 33.1(CH$_2$), 41.0 (CH$_3$) 57.1 (CH$_2$), 61.8 (CH$_2$), 63.0 (CH), 68.4(CH), 70.8 (CH), 72.2 (CH), 73.4 (CH), 93.3 (CH), 119.3 (CH), 127.3 (C), 136.3 (CH), 144.3 (CH), 159.1 (C), 169.5 (C), 169.6 (C), 170.4 (C), 170.8 (C)

MS (%): 509 (M+1)(26), 508 (14), 389 (17), 179(20), 178(19), 177(100) 169(26), 163(24), 109(27), 84(45)

EXAMPLE 3

Synthesis of (S)-(−)-3-(1-methyl-2-pyrrolidinyl)-2-pyridyl β-D-glucopyranoside (9a) and (R)-(+)-3-(1-methyl-2-pyrrolidinyl)-2-pyridyl β-D-glucopyranoside (10a)

In the same procedures as in Example 1, the unpurified diastereomer mixture (5a)(5.0 g) was obtained. The compound (5a) obtained was dissolved in methanol (20 ml). To this solution, ammonia-saturated methanol (10 ml) was added and the resultant solution was stirred at room temperature for 2 hours. The reaction mixture was concentrated under reduced pressure and subjected to silica gel column chromatography using chloroform-/methanol (3:1) as an eluent. As a result, (S)-(−)-3-(1-methyl-2-pyrrolidinyl)-2-pyridyl β-D-glucopyranoside (9a) and (R)-(+)-3-(1-methyl-2-pyrrolidinyl)-2-pyridyl β-D-glucopyranoside (10a) were obtained in white-solid form and in yields of 1.4 g (38%) and 1.3 g (34%), respectively.

<Physical properties of the compound (9a)>
$[\alpha]_D$ −82.7° (c 0.64, MeOH)
UV: $\lambda_{max}$ 219 nm (ε=4,700), 272 nm (ε=4,100)
IR: $\nu(cm^{-1})$; 3356, 2924, 1591, 1437, 1357, 1243, 1052
$^1$H-NMR: δ(CDCl$_3$; ppm from TMS) 1.95–2.05 (3H, m), 2.22 (3H, s), 2.32 (1H, m), 2.39 (1H, q, J=9.1Hz), 3.28 (1H, m), 3.45 (1H, t, J=9.0 Hz), 3.5–3.6 (4H, m), 3.76 (1H, dd, J=5.1, 11.9Hz), 3.93 (1H, dd, J=1.8, 11.9Hz), 5.66 (1H, d, J=7.4Hz), 7.12 (1H, dd, J=5.0, 7.4Hz), 7.82 (1H, dd, J=1.8, 7.4Hz), 8.14 (1H, dd, J=1.8, 5.0Hz),
$^{13}$C-NMR: δ(CDCl$_3$; ppm from TMS); 23.9 (CH$_2$), 31.2 (CH$_2$), 41.0(CH$_3$), 58.1 (CH$_2$), 62.6 (CH$_2$), 68.5 (CH), 71.3 (CH), 74.9 (CH), 77.6 (CH), 78.6 (CH), 99.7 (CH), 120.1 (CH), 126.2 (C), 140.4 (CH), 146.8 (CH), 162.2 (C)
MS (%): 341 (M+1)(1.2), 340 (1.8), 235 (2), 179 (75), 178 (17), 177 (57), 163 (89), 149 (20), 148 (17), 84 (100)
HRMS (high rssolution mass spectrum):
Obs.; 341.1761 cald. for; C$_{12}$H$_{25}$N$_2$O$_6$ (M+1) 341.1713

<Physical properties of the compound (10a)>
$[\alpha]_D$+39.1° (c 0.82, MeOH)
UV: $\lambda_{max}$ 223 nm (ε=2,600), 268 nm (ε=2,800)
IR: $\nu(cm^{-1})$; 3326, 2926, 1591, 1446, 1251, 1075, 754
$^1$H-NMR: δ(CDCl$_3$; ppm from TMS) 1.75 (1H, m), 1.95 (2H, m), 2.36 (3H, s), 2.40 (1H, m), 2.57 (1H, q, J=9.1Hz), 3.41 (1H, m), 3.55 (1H, m), 3.4–3.6 (4H, m) 3.86 (1H, dd, J=4.3, 12.0Hz), 3.99 (1H, m), 5.93 (1H, d, J=7.4Hz), 7.12 (1H, dd, J=5.0, 7.5Hz), 7.90 (1H, dd, J=1.7, 7.5Hz), 8.11 (1H, dd, J=1.7, 5.0Hz)
$^{13}$C-NMR: δ(CDCl$_3$; ppm from TMS); 23.2 (CH$_2$), 33.1 (CH$_2$), 40.8 (CH$_3$) 57.7 (CH$_2$), 62.3 (CH$_2$), 65.1 (CH), 71.0(CH), 74.5 (CH), 78.1 (CH), 78.2 (CH), 97.5 (CH), 119.9 (CH), 125.4 (C), 138.2 (CH), 146.4 (CH), 161.4 (C)
MS (%): 341 (M+1)(1.5), 340 (1.4), 235 (5), 179 (90), 178 (16), 177 (43), 163 (81), 149 (19), 148 (18), 84 (100)
HRMS (high resolution mass spectrum):
Obs.; 341.1720 cald. for; C$_{12}$H$_{25}$N$_2$O$_6$ (M+1) 341.1713

EXAMPLE 4

Synthesis of (S)-(−)-3-(1-methyl-2-pyrrolidinyl)-2-pyridone (2) and (R)-(+)-3-( 1-methyl-2-pyrrolidinyl)-2-pyridone (3) (S)-(−)-3-(1-methyl-2-pyrrolidinyl)-2-pyridyl 2,3,4,6-tetra-O-acetyl-β-D-glucopyranoside (6a)(1.8 g) and (R)-(+)-3-(1-methyl-2-pyrrolidinyl)-2-pyridyl 2,3,4,6-tetra-O-acetyl-β-D-glucopyranoside (7a)(1.7 g) obtained in Example 2 were each dissolved in methanol (20 ml). To each of these solutions, ammonia-saturated methanol (10 ml) was added and the resultant solutions were stirred at room temperature for 2 hours. After the reaction mixtures were concentrated under reduced pressure, methanol (20 ml) was added to each of the mixtures. Further hydrochloric acid (1 ml) was added thereto, and the mixtures were refluxed for 2 hours. After the reaction mixtures were concentrated under reduced pressure, 1N sodium hydroxide solution was added to each residue and the solutions were extracted with ethyl acetate. The extracts were dried over anhydrous magnesium sulfate, filtrated, and the filtrates were concentrated under reduced pressure. As a result, (S)-(−)-3-(1-methyl-2-pyrrolidinyl)-2-pyridone (2) and (R)-(+)-3-(1-methyl-2-pyrrolidinyl)-2-pyridone (3) were obtained in yields of 0.63 g and 0.60 g, respectively. The physical properties of the compounds (2) and (3) obtained were identical to those of the compounds (2) and (3) resolved from the racemic mixture (1) by means of optically active column chromatography.

<Physical properties of the compound (2)>
$[\alpha]_D$ −197° (c 0.93, MeOH)
Melting point: 95.0°–96.0° C.
<Physical properties of the compound (3)>
$[\alpha]_D$ +207° (c 0.89, MeOH)
Melting point: 93.0°–93.5° C.
Properties other than those shown the above, exhibit the same values as shown below.
IR: $\nu(cm^{-1})$; 3136, 2946, 2778, 1647, 1618, 1562, 1477, 1164, 1052, 766
$^1$H-NMR: δ(CDCl$_3$; ppm from TMS) 1.53–1.57 (1H, m), 1.80–1.87 (2H, m), 2.26 (3H, s), 2.40 (2H, m), 3.23 (1H, m), 3.49 (1H, t, J=8.3Hz), 6.34 (1H, dd, J=6.4, 7.0Hz), 7.36 (1H, dd, J=2.0, 6.4H), 7.65 (1H, dd, J=2.0, 7.0Hz)
$^{13}$C-NMR: δ(CDCl$_3$; ppm from TMS); 22.8 (CH$_2$), 33.1 (CH$_2$), 40.8 (CH$_3$) 56.1 (CH$_2$), 64.1 (CH), 107.2 (CH), 132.7 (CH), 134.0 (C), 136.8 (CH), 165.0 (C)
MS (%): 178 (M+)(23), 177 (11), 163 (64), 149 (29), 122 (11), 120 (11), 108 (12), 84 (100), 57 (13)

EXAMPLE 5

Synthesis of (S)-(−)-3-(1-methyl-2-pyrrolidinyl)-2-pyridone (2) and (R)-(+)-3-(1-methyl-2-pyrrolidinyl)-2-pyridone (3) (S)-(−)-3-(1-methyl-2-pyrrolidinyl)-2-pyridyl β-D-glucopyranoside (9a)(1.4g) and (R)-(+)-3-(1-methyl-2-pyrrolidinyl)-2-pyridyl β-D-glucopyranoside (10a)(1.3 g) were each dissolved in methanol (20 ml). To each of these solutions, hydrochloric acid (1 ml) was added and the resultant solutions were refluxed for 2 hours. After the reaction mixtures were concentrated under reduced pressure, 1N sodium hydroxide solution was added to each residue and the solutions were extracted with ethyl acetate. The extracts were dried over anhydrous magnesium sulfate and filtrated, and thereafter concentrated under reduced pressure. As a result, (S)-(−)-3-(1-methyl-2-pyrrolidinyl)-2-pyridone (2) and (R)-(+)-3-(1-methyl-2-pyrrolidinyl)-2-pyridone (3) were obtained in yields of 0.73 g and 0.68 g, respectively. The physical properties of the compounds (2) and (3) obtained were identical to those of the compounds (2) and (3) resolved from racemic mixture (1) by means of optically active column chromatography.

As shown hereinabove, in accordance with the present invention, (S)-(−)-3-(1-methyl-2-pyrrolidinyl)-2-pyridone (2) and (R)-(+)-3-(1-methyl-2-pyrrolidinyl)-2-pyridone (3) were successfully resolved from the racemic mixture (1) in a high yield.

As an analogue of the optically active compounds (2) and (3) successfully resolved in accordance with the method of the present invention, nicotine may be mentioned. Nicotine is known to have physiological activities including autonomic regulation, circulatory regulation such as blood pressure activation, and digestive regulation such as gastrointestinal activation [Biochemistry, 57, 447 (1985); J. Pharm, Experi. Ther., 222, 463 (1983); Br. J. Pharmac., 79, 869 (1983)]. A nicotine derivative also has a physiological activity. For example, alkoxynicotine is known to have antimicrobial and antibacterial activities (U.S. patent Ser. No. 3,644,176). As mentioned above, nicotine or the nicotine derivative possesses various physiological activities and are expected to be utilized as medicinal agents. Further, nicotine and the nicotine derivative are expected to be applied in the field of agriculture based on the fact that a nicotine sulfate has been utilized as an agricultural insecticide.

As described above, nicotine and the nicotine derivative have many possible usages and the method of the present invention is an efficient process for obtaining the nicotine derivatives (2) and (3) at a low cost and with high selectivity.

What is claimed is:

1. A method of optically resolving (±)-3-(1-methyl-2-pyrrolidinyl)-2-pyridone (1) into (S)-(−)-3-(1-methyl-2-pyrrolidinyl)-2-pyridone (2) and (R)-(+)-3-(1-methyl-2-pyrrolidinyl)-2-pyridone (3), which comprises the steps of
   (i) obtaining a nicotine glycoside (5), which is a diastereomer mixture, from (±)-3-(1-methyl-2-pyrrolidinyl)-2-pyridone (1) and a monosaccharide or a disaccharide of hexose (4) as shown below:

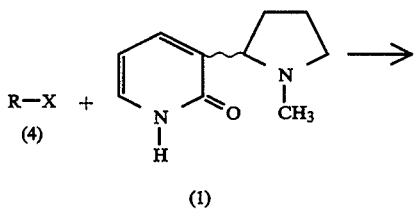

(1)

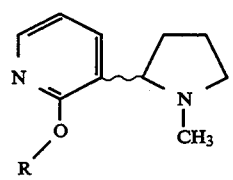

(5)

wherein R is a monosaccharide or a disaccharide of hexose whose hydroxyl group is protected by an acyl group, and X is an active unit;
   (ii) obtaining compounds (6) and (7) by resolving said nicotine glycoside (5) by means of column chromatography as shown below:

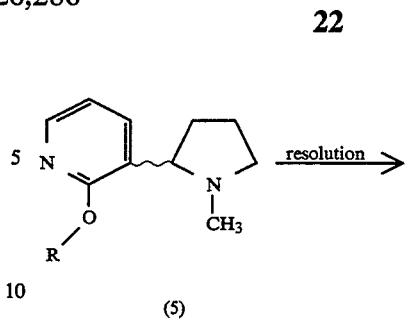

(5)

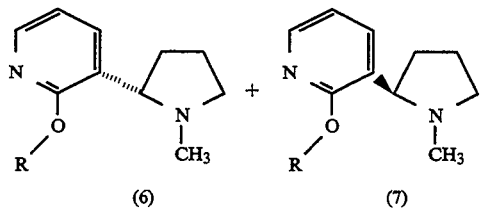

(6) (7)

wherein R is defined hereinabove; and
   (iii) obtaining (S)-(−)-3-(1-methyl-2-pyrrolidinyl)-2-pyridone (2) and (R)-(+)-3-(1-methyl-2-pyrrolidinyl)-2-pyridone (3) by treating said compounds (6) and (7) under an acidic condition as shown below:

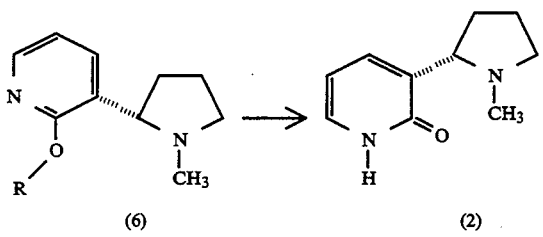

(6) (2)

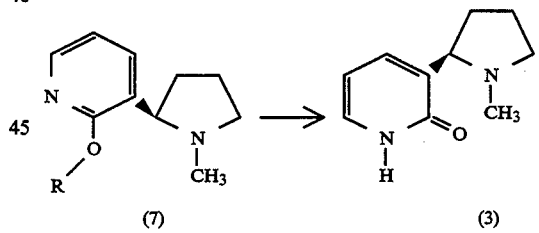

(7) (3)

wherein R is defined hereinabove.

2. The method according to claim 1, wherein said step (iii) is replaced by the following step in which the compounds (6) and (7) obtained in said step (ii) are deprotected under a basic condition, and thereafter, treated under an acidic condition to obtain the compounds (2) and (3) as shown below:

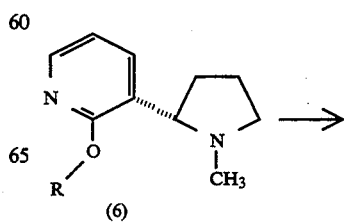

(6)

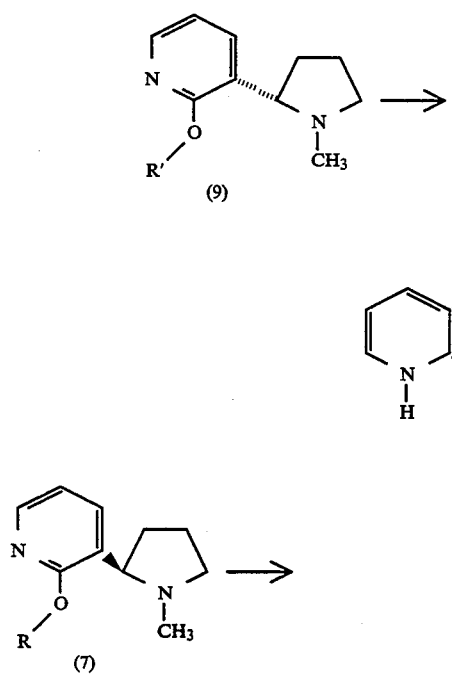

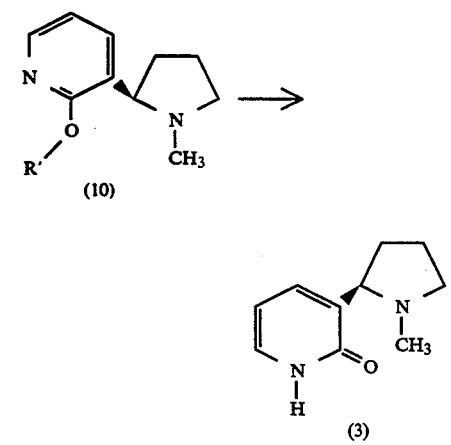

wherein R is as defined in claim 1 and R' is a monosaccharide or a disaccharide of hexose whose hydroxyl group is not protected.

3. The method according to claim 1, further comprising the following steps (iv) to (vi) which are performed after said step (i):

(iv) obtaining a nicotine glycoside (8), which is a diastereomer mixture, by removing the protecting group of the sugar part of said nicotine glycoside (5) under an alkaline condition as shown below:

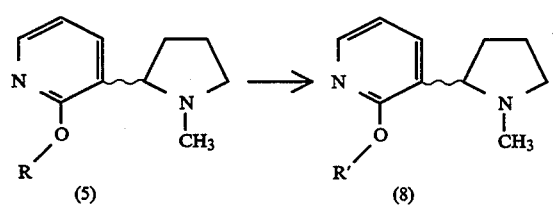

wherein R and R' are as defined in claims 1 and 2, (v) obtaining compounds (9) and (10) by resolving said nicotine glycoside (8) by means of column chromatography as shown below:

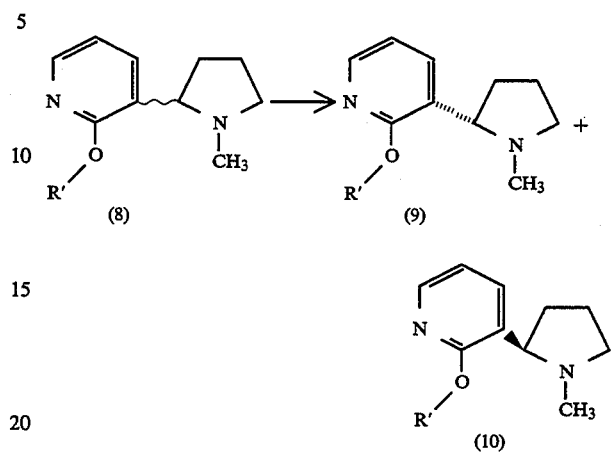

wherein R' is as defined in claim 2, and (vi) a step of obtaining (S)-(−)-3-(1-methyl-2-pyrrolidinyl)-2-pyridone (2) and (R)-(+)-3-(1-methyl-2-pyrrolidinyl)-2-pyridone (3) by treating the compounds (9) and (10) under an acidic condition as shown below:

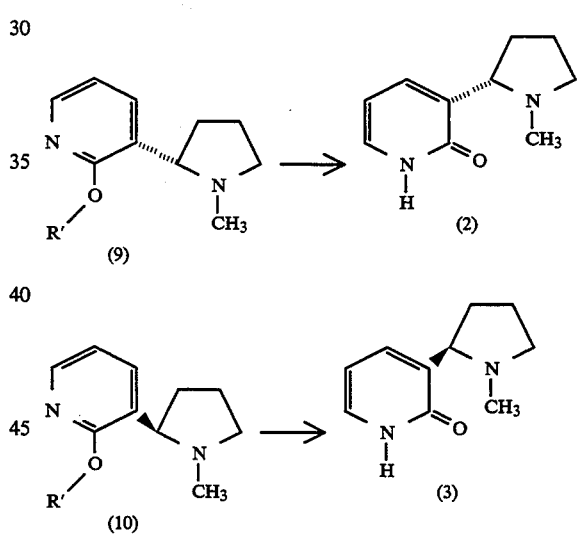

wherein R' is as defined in claim 2.

4. The method according to any one of claims 1 to 3, wherein the R group of said nicotine glycoside is selected from the group consisting of glucopyranosyl group, galactopyranosyl group, a mannopyranosyl group, a lactosyl group, a manntosyl group, and a cellobiosyl group whose hydroxyl groups are protected by an acyl group.

5. The method according to any one of claims 1 to 3, wherein the R group of said nicotine glycoside is selected from the group consisting of a 2,3,4,6-tetra-O-acylglucopyranosyl group, a 2,3,4,6-tetra-O-acylgalactopyranosyl group, and a 2,3,4,6-tetra-O-acylmannopyranosyl group.

6. The method according to any one of claims 1 to 3, wherein said acyl group is selected from the group consisting of an acetyl group, a pivaloyl group, a benzoyl group, and a toluoyl group.

7. The method according to claim 4, wherein said acyl group is selected from the group consisting of an acetyl group, a pivaloyl group, a benzoyl group, and a toluoyl group.

8. The method according to claim 5, wherein said acyl group is selected from the group consisting of an acetyl group, a pivaloyl group, a benzoyl group, and a toluoyl group.

9. The method according to any one of claims 1 to 3, wherein the R group of said nicotine glycoside is a 2,3,4,6-tetra-O-acetyl-β-D-glucopyranosyl group.

10. The method according to any one of claims 1 to 3, wherein said column chromatography is selected from the group consisting of optically active column chromatography, ODS reversed phase column chromatography, alumina column chromatography, and silica gel column chromatography.

11. The method according to any one of claims 1 to 3, wherein the treatment for cleaving a glycosidic bond under said acidic condition is carried out in the presence of an acid selected from the group consisting of hydrochloric acid, sulfuric acid, and nitric acid.

12. The method according to claims 2 or 3, wherein said treatment for deprotecting an acyl group under said basic condition is carried out in the presence of a base selected from the group consisting of sodium methoxide, sodium hydroxide, and ammonia.

13. The method according to claim 1 wherein the active unit X is a halogen atom.

* * * * *